United States Patent [19]

Ootsu

[11] Patent Number: 5,250,296
[45] Date of Patent: Oct. 5, 1993

[54] IMMUNOSTIMULANT AGENT CONTAINING INTERLEUKIN-2 AND 5′-DEOXY-5-FLUOROURIDINE

[75] Inventor: Koichiro Ootsu, Osaka, Japan

[73] Assignee: Takeda Chemical Industries, Ltd., Osaka, Japan

[21] Appl. No.: 800,366

[22] Filed: Nov. 27, 1991

[30] Foreign Application Priority Data

Nov. 29, 1990 [JP] Japan .................. 2-325475

[51] Int. Cl.$^5$ .................. A61K 37/02; A61K 45/05
[52] U.S. Cl. .................. 424/85.2; 536/28.55; 514/50
[58] Field of Search .................. 424/85.2; 536/24; 514/50

[56] References Cited

U.S. PATENT DOCUMENTS 4,518,584  5/1985  Mark et al. .................. 424/85

FOREIGN PATENT DOCUMENTS

| | | |
|---|---|---|
| 0154316 | 2/1982 | European Pat. Off. . |
| 0091539 | 10/1983 | European Pat. Off. . |
| 0145390 | 6/1985 | European Pat. Off. . |
| 0176299 | 4/1986 | European Pat. Off. . |
| 0228833 | 7/1987 | European Pat. Off. . |
| 60-126088 | 3/1981 | Japan . |

OTHER PUBLICATIONS

Nihomiya et al Gan to Kagaku Ryoho 14(12) pp. 3271-3277, (Dec. 1987) (Abstract only).
Fujita et al Gan to Kagaku Ryoho 14(5 pt 1) pp. 1297-1304, (May 1987) (Abstract only).
Corbett et al Cancer vol. 40, No. 5 Nov. 1977, pp. 2660-2680.
Japanese Journal of Cancer and Chemotherapy, vol. 13, No. 4, 1986 plus English translation.
Japanese Journal of Cancer and Chemotherapy vol. 12, No. 9, 1985, plus English translation.
G. Mills et al. Generation of Cytotoxid Lymphocytes to Syngeneic Tumors by Using Do–Stimulator Interluekin 2: In Vivo Activity, J. Immunology, vol. 125 p. 1904 (1980).
S. Rosenberg et al., A Progress Report on the Treatment of 157 Patients with Advanced Cancer Using Lymphokine-Activated Killer Cells and Interleukin-2 or High-Dose Interluekin-2 Alone, N.E. J. of Medicine, vol. 316 pp. 889-897 (1987).
A. Cook et al, Fluorinated Pyrimidine Nucleosides. 3.$^1$ Synthesis and Antitumor Activity of a Series of 5′-Deoxy-5-fluropyrimidine Nucleosides, J. of Medicinal Chem., vol. 22, pp. 1330-1335 (1979).
Y. Ninomiya et al, Cancer and Chemotherapy, 15 (5), 1747-1754. (Abstract only).

*Primary Examiner*—Michael G. Wityshyn
*Assistant Examiner*—Choon P. Koh
*Attorney, Agent, or Firm*—David G. Conlin; Ronald I. Eisenstein

[57] ABSTRACT

Disclosed is an immunostimulant agent containing interleukin-2 and 5′-deoxy-5-fluorouridine or a salt thereof in combination, which shows a strong therapeutic effect by synergistic action and weak side effects. The immunostimulant agent may further contain another chemotherapeutic agent and/or another immunotherapeutic agent.

19 Claims, No Drawings

5,250,296

IMMUNOSTIMULANT AGENT CONTAINING INTERLEUKIN-2 AND 5'-DEOXY-5-FLUOROURIDINE

BACKGROUND OF THE INVENTION

The present invention relates to an immunostimulant agent, and more particularly to a clinically applicable immunostimulant agent containing interleukin-2 (hereinafter also briefly referred to as IL-2) and 5'-deoxy-5-fluorouridine (generic name: doxifluridine, hereinafter also briefly referred to as 5'-DFUR).

Attempts have been made in recent years, as immunostimulant agent and various viral infections, by using the so-called lymphokines such as IL-2 for immunopotentiation [J. Immunol., 125, 1904 (1980)]. Recently, IL-2 obtained by genetic engineering technique has been known (Japanese Patent Unexamined Publication Nos. 60-115528/1985 and 61-78799/1986).

On the other hand, 5'-DFUR was synthesized in 1979, and the effectiveness thereof in clinical tests was discovered [Cancer and Chemotherapy 12(1), 2044 (1985)]. For this reason, 5'-DFUR has recently been on the market.

At present, cancer has been tried to be treated by operative therapy, radiotherapy and hormonotherapy, which are effective against primary cancer. However, metastasized cancer and too late discovered cancer cannot be so treated, therefore, pharmacotherapy is used. Anticancer drugs currently usable exhibit a useful effect, but have strong side effects on organisms. Pharmacotherapy is not completely satisfactory as therapy for patients.

In recent years, lymphokines such as IL-2 have been used as antitumor agents to treat human malignant tumors [Cancer and Chemotherapy 13, 977 (1986)], and therapeutic effects thereof have also been reported [New England J. Med. 316, 889 (1987)].

SUMMARY OF THE INVENTION

The present inventors have hitherto conducted various investigations into the therapy of administering immunotherapeutic agents in combination with chemotherapeutic agents and IL-2 to enhance immunostimulant effects on malignant neoplasms. As a result, the present inventors discovered the fact that the administration of 5'-DFUR in combination with IL-2 to cancer-carrying animals exhibits each function co-operatively and gives a strong therapeutic effect.

The present invention provides:

(1) in one embodiment, a method for immunostimulating a mammal, which comprises administering an effective amount of interleukin-2 and 5'-deoxy-5-fluorouridine or a salt thereof, (2) in another embodiment, a pharmaceutical composition for immunostimulating a mammal which comprises an effective amount of interleukin-2 and 5'-deoxy-5-fluorouridine or a salt thereof in a pharmaceutical carrier, (3) in another embodiment, the combination of interleukin-2 and 5'-deoxy-5-fluorouridine or a salt thereof for the manufacture of a medicament for immunostimulating a mammal, (4) in still another embodiment, a method for producing a pharmaceutical composition for immunostimulating a mammal, which comprises using interleukin-2 and 5'-deoxy-5fluorouridine or a salt thereof, and (5) in more still another embodiment, a kit of pharmaceutical preparations for immunostimulating a mammal, which comprises a pharmaceutical preparation of interleukin-2 and a phamaceutical preparation of 5'-deoxy-5-fluorouridine.

DESCRIPTION OF THE PREFERRED EMBODIMENTS

As the above-mentioned IL-2, any substance may be used, as long as it has IL-2 activity, namely the activity of enabling to promote and maintain in vitro long-term cultures of T cells while keeping their functions.

Examples of such substances include natural IL-2 produced in animal bodies or animal cells, IL-2 produced by recombinant technology and their related substances. When the IL-2 described above and the related substances thereof are proteins, they may have sugar chains or not.

Specific examples thereof include polypeptide (I) (human IL-2) having the amino acid sequence shown in SEQ ID NO:1 (SEQ ID NO: 1) and a fragment having a portion of the amino acid sequence necessary for its biological or immunological activity. Examples of the above-mentioned fragments include a fragment lacking one amino acid residue at the amino terminus (European Patent Publication No. 91539), a fragment lacking 4 amino acid residues at the amino terminal portion (Japanese Patent Unexamined Publication No. 60-126088/1985) and a fragment lacking several amino acid residues at the carboxyl terminal portion (Japanese Patent Unexamined Publication No. 60-126088/1985). Further, a portion of the constituent amino acid residues of polypeptide (1) having the amino acid sequence shown in SEQ ID NO:1 may be deleted or substituted with a different amino acid residue(s). For example, the cystine residue at the 125-position may be substituted with a serine residue (Japanese Patent Unexamined Publication No. 59-93093/1984 which corresponds to U.S. Pat. No. 4,518,584).

The above-mentioned IL-2 may be chemically modified, for example with a polyetylene glycol derivative (e.g. Japanese Patent Unexamined Publication No. 60-226821/1985 which corresponds to European Publication No. 154316).

In particular, human IL-2 produced by genetic engineering technique and having the amino acid sequence shown in SEQ ID NO:1 is preferably used in the present invention. In this case, the human IL-2 may be a mixture of the IL-2 further having a methionine (Met) residue at its amino terminus and the IL-2 having no methionine as its amino terminus residue (Japanese Patent Unexamined Publication Nos. 60-115528/1985 which corresponds to European Publication No. 145390 and 61-78799/1986 which corresponds to European Pulication No. 176299), or may have no methionine residue at its amino terminus and start with an alanine (Ala) residue (Japanese Patent Unexamined Publication No. 61-78799/1986 which corresponds to European publication No. 176,299). Further, the IL-2 may have a sugar chain.

5'-DFUR is a known compound, which is described in J. Med. Chem. 22, 1330–1335 (1979), and produced by a method using 5-fluorouridine as a starting material as described therein.

5'-DFUR is known to have low toxicity to animals, and particularly its effect is reported in [Cancer and Chemotherapy 15(5), 1747–1754 (1988)].

IL-2 enhances the reactivity of lymphoid cells, thereby exhibiting its biological activity. It is therefore desirable that IL-2 is combined with an anticancer agent lower in immunosuppressive activity. 5'-DFUR is a drug fit for this purpose.

The IL-2 used in the present invention is low in toxicity. For example, even when human IL-2 having the amino acid sequence shown in SEQ ID NO:1 (which is obtained by separating a mixture of the IL-2 further having a methionine (Met) residue at its amino terminus and the IL-2 having no methionine residue at its amino terminus by an isoelectric focusing method similar to that described in Japanese Patent Unexamined Publication No. 61-78799/1986 which corresponds to European Publication No. 176,299) is given intravenously to mice or rats in a dose of 10 mg/kg (1 mg=$3.5 \times 10^4$ units), no mice or no rats die of its toxicity.

5'-DFUR used in the present invention is low in toxicity as compared to other known chemotherapeutic agents. For example, even when 5'-DFUR is given to mice orally in a dose of 2,000 mg/kg or intraperitoneally in a dose of 500 mg/kg, no mice die. Also, when 5'-DFUR is given to organisms, it does not inhibit the activity of natural killer cells. In accordance with this invention, this compound, which does not inhibit the activity, is very suitable for administration in combination with IL-2.

Thus, the immunostimulant agents of the present invention are usually given orally or parenterally as pharmaceutical preparations containing these active ingredients and pharmaceutically acceptable carriers or excipients. For example, forms of the formulations include an aqueous solution in which each active ingredient is previously dissolved or a solid mixture obtained by lyophilization of each active ingredient or a mixture in which each solid is obtained by lyophilization of each solution containing each active ingredient or a combination of an aqueous solution in which one of the active ingredients is dissolved and a solid obtained by lyophilization of the other.

The immunostimulant agent of the present invention can be given as one preparation formulated by mixing these active ingredients and a pharmaceutically acceptable diluent, excipient, etc. if necessary, in accordance with pharmaceutical manufacturing methods known in the art. Further, the respective active agents are separately formulated using a pharmaceutically acceptable diluent, excipient, etc. if necessary, prepared as a kit of pharmaceutical preparations which comprises a pharmaceutical preparation of IL-2 and a pharmaceutical preparation of 5'-DFUR, and can be given as respective one preparation using a diluent, etc. when used. Furthermore, the respective active agents are separately formulated as described above, prepared as a kit of phamaceutical preparations and can be given to the same object separately, concurrently or at time intervals, through the same route or different routes. When the immunostimulant agents of the present invention are used in solution form, they are prepared by conventional methods, using solvents such as aqueous solvents (for example, distilled water), water-soluble solvents (for example, physiological saline and Ringer solution) and oil-soluble solvents (for example, sesame oil and olive oil). Additives can be added such as solubilizing adjuvants (for example, sodium salicylate and sodium acetate), buffers (for example, sodium citrate and glycerin), isotonic agents (for example, glucose and invert sugar), stabilizers (for example, human serum albumin and polyethylene glycol), preservatives (for example, benzyl alcohol and phenol) and soothing agents (for example, benzalkonium chloride and procaine hydrochloride) if necessary.

The concentration of IL-2 in the solution is preferably about 3 to about 500 mg/ml.

The concentration of 5'-DFUR in the solution is preferably about 10 to about 500 mg/ml.

Formulations for oral administration include, for example, tablets, pills, granules, powders, capsules, syrups, emulsions and suspensions. Such formulations are prepared by known methods, and lactose, starch, sucrose, magnesium stearate, etc. are used as the carriers or the excipients.

For parenteral administration, for example, injections and suppositories can be used. Examples of the injections which can be used include intravenous injections, subcutaneous injections, intradermic injections, intramuscular injections and drops. The injections are usually provided, with ampules charged with them. The suppositories for intrarectal administration are prepared by known methods.

When the immunostimulant agent of the present invention is formulated, it is desirable to add about 0.5 to 1% of human serum albumin (HSA) to prevent the activity of IL-2 from being lowered, as described in Japanese Patent Unexamined Publication No. 62-228026/1987 which corresponds to European Publication No. 228,833. For example, a mixture of respective materials can be dissolved in distilled water or in physiological saline for injection.

The immunostimulant agents of the present invention are useful for treatment or prophylaxis of tumors of mammals such as mice, cats, dogs, cattle, horses, sheep, goats, rabbits and humans, and have a remarkable effect, for example, on apothanasia of mammals carrying tumors. Such subject diseases include leukemia of various kinds, malignant lymphoma, osteosarcoma, malignant melanoma, malignant choriocarcinoma, myosarcoma, ovary cancer, uterus cancer, prostate cancer, pancreatic carcinoma, cancer of digestive organs such as the stomach and the intestine, lung cancer, esophageal carcinoma, head and neck tumor and brain tumor.

When the formulations of the immunostimulant agents of the present invention are in solution form, such solutions are suitable for injection.

When the solid formulations obtained by lyophilization are used, they are dissolved in distilled water or physiological saline to use them as solutions for injection. The formulations may also be dissolved in solutions containing monosaccharides, sugar alcohols, amino acids, etc. as described above and pH adjusted as described above, if necessary, and then they may be used.

In giving the immunostimulant agents of the present invention, the amounts of IL-2 and 5'-DFUR used vary depending on the method for administration, the subject tumor, etc. However, 5'-DFUR is used preferably in an amount of about 0.1 to about 100 mg per 10 $\mu$g (350 units as IL-2 activity) of protein of IL-2, and more preferably in an amount of about 1 to 50 mg. IL-2 activity is assayed using a mouse cell strain which proliferates depending on the IL-2 concentration as described in Japanese Patent Unexamined Publication No. 60-115528/1985 which corresponds to European Publication No. 145,390. The immunostimulant agents of the present invention can be given to mammals including humans orally or parenterally. The dosage of the immunostimulant agents of the present invention varies according to the kind of IL-2 used. For example, when the immunostimulant agents are given as injections, based on the protein amount of IL-2, it is preferred that they are given to mice in a dosage of about 0.1 to 500 μg and to mammals other than mice in a dosage of about 0.001 to 4 μg. When the immunostimulant agents are given as suppositories, drops and oral agents, the dosages are preferably about 0.01 to 20 μg/kg, about 0.001 to 2 μg/kg and about 0.2 to 4 μg/kg, respectively. On the other hand, when the immunostimulant agents are given as injections, based on the dosage (mg) of 5'-DFUR, they are given to mice, for example, in a dosage of about 1 to 500 mg/kg daily, and to mammals other than mice in a dosage of about 1 to 100 mg/kg daily.

For the immunostimulant agents of the present invention, IL-2 and 5'-DFUR separately formulated can be given to the same object concurrently or at time intervals. The time interval in this case may be, for example, about 12 to 24 hours, preferably about 3 to 9 hours and more preferably about 2 hours or less.

The immunostimulant agent of the present invention may further contain another chemotherapeutic agent and/or another immunotherapeutic agent. The chemotherapeutic agents include anticancer agents such as mitomycin, adriamycin, cisplatin, vindesine, vincristine, cyclophosphamide, ifosfamide, bleomycin, peplomycin and etoposide. The immunotherapeutic agents include microorganisms or bacterial cell wall skeletal components; immunologically active natural polysaccharides or cytokines obtained by genetic engineering technique; and colony stimulating factor. The above-mentioned immunologically active polysaccharides include lenthinan and schizophyllan. The bacterial cell wall skeletal components include muramyldipeptide derivatives, and the microorganisms include lactic acid bacteria. The natural cytokines or the cytokines obtained by genetic engineering technique include interferons.

When another chemotherapeutic agent and/or another immunotherapeutic agent is added to the immunostimulant agent of the present invention, it is used in an amount usually employed for treatment.

The combination of IL-2 and 5'-DFUR having low immunosuppressive activity provides the immunostimulant agents which have synergistic effect and weak side effects.

The agents of the present invention comprising IL-2 and 5'-DFUR exhibit a remarkable immunostimulant activity such as antitumor activity and macrophage activation activity which cannot be obtained by independent use of each component. It is preferable that the present immunostimulant agent is used for treating a mammal containing at least one tumor.

The present invention will hereinafter be described in detail with the following Experimental Examples and Examples. It is understood of course that these Experimental Examples and Examples are not intended to limit the scope of the invention.

The IL-2 used in Experimental Examples and Examples is human IL-2 having the amino acid sequence shown in SEQ ID NO:1, namely IL-2 having the amino terminus starting with an alanine residue. The IL-2 is prepared by cultivating transformant *E. coli* N4830/pTB285 (IFO 14437, FERM BP-852) by a method similar to that described in Japanese Patent Unexamined Publication No. 61-78799/1986 which corresponds to European Publication No. 176299, highly purifying the cultivated product by a method similar to that described in Japanese Patent Unexamined Publication No. 60-115528/1985 which corresponds to European Publication No. 145390, and isolating the IL-2 by an isoelectric focusing method similar to that described in Japanese Patent Unexamined Publication No. 61-78799/1986 which corresponds to European Publication No. 176299. The specific activity thereof is about $5 \times 10^4$ units/mg.

Transformant *E. coli* N4830/pTB285 described above was deposited with the Institute for Fermentation, Osaka, Japan (IFO) under the accession number IFO 14437 on Apr. 25, 1985. This microorganism was also deposited with the Fermentation Research Institute, the Agency of Industrial Science and Technology, the Ministry of International Trade and Industry, Japan (FRI) under the accession number FERM P-8199 on Apr. 30, 1985. This deposit was converted to the deposit under the Budapest Treaty and the microorganism has been stored at FRI under the accession number BP-852.

EXPERIMENTAL EXAMPLE 1

Comparative Experiment on Antitumor Activity of 5'-DFUR, IL-2 and Combination of 5'-DFUR and IL-2 to Subcutaneously Implanted Tumor Tissue gruel (tumor cells ground by a homogenizer to a suspended state) of mouse colon carcinoma 26 (colic cancer No. 26) was subcutaneously implanted through an injection tube in sural regions of hind-limbs of male BALB/c mice with a body weight of about 25 g. Twelve days after the tumor implantation, mice in which tumors grew to a predetermined size were selected and divided into groups, and drug administration was initiated. IL-2 was subcutaneously given to lateral abdominal region opposite to the tumor-implanted hind-limb once a day continuously for 14 days. IL-2 was dissolved in physiological saline (dissolving solution) containing 5% of normal mouse serum so that the resulting solution was given in an amount of 0.1 ml/20 g of body weight of mouse. 5'-DFUR was orally given to the mice once a day from the first day of the IL-2 administration for 14 days. 5'-DFUR was suspended in physiological saline so that the resulting solution was given in an amount of 0.2 ml/20 g of body weight of mouse. The antitumor effect was evaluated by measuring the weight of tumors 28 days after the tumor implantation, determining the average weight of the tumors of each experimental group, and determining the tumor weight ratio (T/C %) of the group of mice treated with the drug (T, 5 mice per group) to the group of mice untreated with the drug (C, 10 mice per group). The daily dosage of the drugs is shown by the weight of the drugs (IL-2: μg, 5'-DFUR: μg) per mouse. Experimental results are shown in Table 1.

TABLE 1

| Dosage (μg/mouse/day) | | Number of mice | Tumor Weight (mg) average ± SD | Weight ratio of tumor (T/C %) | Increase in body weight (g) (12-22 days) |
|---|---|---|---|---|---|
| 5'-DFUR | IL-2 | | | | |
| Untreated control | | 10 | 1105 ± 130 | | 2.2 |
| 0 | 20 | 5 | 532 ± 151 | 48 | 1.8 |
| 1000 | 0 | 5 | 777 ± 12 | 70 | 2.2 |
| 1000 | 20 | 5 | 311 ± 74 | 28 | 0.9 |
| 2000 | 0 | 5 | 353 ± 153 | 32 | 0.9 |
| 2000 | 20 | 5 | 55 ± 25 | 5 | −1.7 |

EXPERIMENTAL EXAMPLE 2

Comparative Experiment on Antitumor Activity of 5'-DFUR. IL-2 and Combination of 5'-DFUR and IL-2 to Subcutaneously Implanted Tumor Tissue gruel of colic cancer No. 26 prepared similarly with Experimental Example 1 was subcutaneously implanted in lateral abdominal regions of female BALB/c mice with a body weight of about 20 g by use of an injection tube. Seven days after the tumor implantation, mice in which tumors grew to a predetermined size were selected and divided into groups, and drug administration was initiated. IL-2 was subcutaneously given to lateral abdominal region opposite to the tumor-implanted sites once a day continuously for 15 days. 5'-DFUR was orally given to the mice once a day from the first day of the IL-2 administration, 14 times in total. IL-2 was dissolved in physiological saline (dissolving solution) containing 5% of normal mouse serum so that the resulting solution was given in an amount of 0.1 ml/20 g of body weight of mouse. 5'-DFUR was suspended in physiological saline so that the resulting solution was given in an amount of 0.2 ml/20 g of body weight of mouse. The antitumor effect was evaluated by measuring the weight of tumors 28 days after the tumor implantation, determining the average weight of the tumors of each experimental group, and determining the tumor weight ratio (T/C %) of the group of mice treated with the drug (T, 5 mice per group) to the group of mice untreated with the drug (C, 10 mice per group). The daily dosage of IL-2 is shown by the weight (μg) of the drug per mouse, and the daily dosage of 5'-DFUR is also shown by the weight (μg) of the drug per mouse. Results obtained by giving IL-2 alone and a combination of IL-2 and 5'-DFUR of the present invention are shown in Table 2.

TABLE 2

| Dosage (μg/mouse/day) | | Number of mice | Tumor weight (mg) average ± SD | Weight ratio of tumor (T/C %) | Increase in body weight (g) (7-21 days) |
|---|---|---|---|---|---|
| 5'-DFUR | IL-2 | | | | |
| Untreated control | | 10 | 2382 ± 331 | | 2.4 |
| 0 | 20 | 5 | 2520 ± 370 | 106 | 3.6 |
| 2000 | 0 | 5 | 1562 ± 404 | 66 | 3.6 |
| 2000 | 20 | 5 | 123 ± 147 | 5 | 1.2 |

EXPERIMENTAL EXAMPLE 3

Examination of Tumor Activity to Subcutaneously Implanted Tumor by Combination of 5'-DFUR and IL-2 with Another Anticancer Agent Tissue gruel of colic cancer No. 26 was subcutaneously implanted in abdominal regions of female BALB/c mice with a body weight of about 20 g, similarly with Experimental Example 2. 5'-DFUR and IL-2 were given once a day continuously 10 times from 14 days after the tumor implantation. 5'-DFUR was orally given, and IL-2 was subcutaneously given to abdominal region opposite to the tumor-implanted site as with Experimental Example 2. Anticancer agents, mitomycin (hereinafter referred to as MMC), adriamycin (hereinafter referred to as ADR) and cyclophosphamide (hereinafter referred to as CPA), were intravenously given to the mice 7 and 10 days after the tumor implantation. The dosage of each drug is shown by the weight (μg) per mouse. Even when 5'-DFUR and IL-2 of the present invention were only given for 10 days after the tumors had grown, excellent effect could be exhibited by the combinations with the additional anticancer agents. Results (the tumor weight 28 days after the tumor implantation) are shown in Table 3.

TABLE 3

| | Dosage (μg/mouse/day) | | | Number of mice | Tumor weight (mg) average ± SD |
|---|---|---|---|---|---|
| Anticancer agent | 5'-DFUR | IL-2 | | | |
| Untreated control | | | | 10 | 2320 ± 783 |
| | 0 (*) | 0 () | 0 (*) | 5 | 1967 ± 511 |
| | 0 | 2000 | 20 | 5 | 1138 ± 224 |
| MMC | 60 | 0 | 0 | 5 | 1445 ± 130 |
| MMC | 60 | 2000 | 20 | 5 | 275 ± 210 |
| ADR | 100 | 0 | 0 | 5 | 1902 ± 165 |
| ADR | 100 | 2000 | 20 | 5 | 171 ± 70 |
| CPA | 1000 | 0 | 0 | 5 | 1580 ± 149 |
| CPA | 1000 | 2000 | 20 | 5 | 118 ± 116 |

| | Dosage (μg/mouse/day) | | | Weight ratio of tumor (T/C %) | Increase in body weight (g) (14-28 days) |
|---|---|---|---|---|---|
| Anticancer agent | 5'-DFUR | IL-2 | | | |
| Untreated control | | | | | 2.9 |
| | 0 (*) | 0 () | 0 (*) | 85 | 1.7 |
| | 0 | 2000 | 20 | 49 | |
| MMC | 60 | 0 | 0 | 62 | 1.7 |
| MMC | 60 | 2000 | 20 | 12 | 1.0 |
| ADR | 100 | 0 | 0 | 82 | 1.7 |
| ADR | 100 | 2000 | 20 | 7 | 1.5 |
| CPA | 1000 | 0 | 0 | 68 | 1.6 |
| CPA | 1000 | 2000 | 20 | 5 | 1.7 |

*Physiological saline was intravenously given in an amount of 0.2 ml/20 g.
**Physiological saline was orally given in an amount of 0.2 ml/20 g.
***The solvent (5% normal mouse serum-containing physiological saline) for IL-2 was subcutaneously given in an amount of 0.1 ml/mouse.

EXPERIMENTAL EXAMPLE 4

Comparative Experiment on Survival Effect of 5'-DFUR, IL-2 and Combination of 5'-DFUR and IL-2 to Subcutaneously Implanted Tumor Tissue gruel of colic cancer No. 26 prepared similarly with Experimental Example 1 was subcutaneously implanted through an injection tube in femoral regions of male BALB/c mice with a body weight of about 25 g. Twenty days after the tumor implantation, mice in which tumors grew to a predetermined size were selected and divided into groups, and drug administration was initiated. IL-2 was subcutaneously given to lateral abdominal region opposite to the tumor-implanted site once a day continuously for 15 days. 5'-DFUR was orally given to the mice once a day from the day of the IL-2 administration, 15 times in total. IL-2 was dissolved in physiological saline (dissolving solution) containing 5% of normal mouse serum so that the resulting solution was given in an amount of 0.1 ml/20 g of body weight of mouse. 5'-DFUR was suspended in Physiological saline so that the resulting solution was given in an amount of 0.2 ml/20 g of body weight of mouse. The antitumor effect was evaluated by observing the survival time of the tumor-carrying mice, determining the average (median) survival time of each experimental group, and determining the survival time ratio (T/C %)

of the group of mice treated with the drug (T, 5 mice per group) to the group of mice untreated with the drug (C, 5 mice per group). The daily dosage of IL-2 is shown by the weight (μg) of the drug per mouse, and the daily dosage of 5'-DFUR is also shown by the weight (μg) of the drug per mouse. Results obtained by giving IL-2 alone and a combination of IL-2 and 5'-DFUR of the present invention are shown in Table 4.

TABLE 4

| Drug | Dosage (μg/ mouse) | Number of mice | Survival time (days) | average (median) | T/C (%) |
|---|---|---|---|---|---|
| Untreated control | | 5 | 33, 35, 35, 41, 56 | 35.5 | |
| IL-2 | 10 | 5 | 41, 42, 43, 45, 56 | 43.5 | 123 |
| 5'-DFUR | 2000 | 5 | 46, 52, 56, 69, 76 | 56.5 | 159 |
| 5'-DFUR + IL-2 | | 5 | 85, 87, >93*, >93, >93 | >92.8 | >262 |

*>93: The mouse was slaughtered 93 days after the tumor implantation. The tumor completely disappeared.

EXPERIMENTAL EXAMPLE 5

Comparative Experiment on Survival Effect of 5'-DFUR, IL-2 and Combination of 5'-DFUR and IL-2 to Subcutaneously Implanted Tumor by Different Schedule Tissue gruel of colic cancer No. 26 prepared similarly with Experimental Example 1 was subcutaneously implanted through an injection tube in femoral regions of male BALB/c mice with a body weight of about 25 g. Fourteen days after the tumor implantation, mice in which tumors grew to a predetermined size were selected and divided into groups, and drug administration was initiated. The subcutaneous administration of IL-2 to lateral abdominal region opposite to the tumor-implanted site was done once a day for 4 continuous days each week and was repeated for 5 weeks. The oral administration of 5'-DFUR to the mice is done once a day for 4 continuous days of each week starting on the first day of the IL-2 administration and was repeated for 5 weeks. IL-2 was dissolved in physiological saline (dissolving solution) containing 5% of normal mouse serum so that the resulting solution was given in an amount of 0.1 ml/20 g of body weight of mouse. 5'-DFUR was suspended in physiological saline so that the resulting solution was given in an amount of 0.2 ml/20 g of body weight of mouse. The antitumor effect was evaluated by observing the survival time of the tumor-carrying mice, determining the average (median) survival time of each experimental group, and determining the survival time ratio (T/C %) of the group of mice treated with the drug (T, 5 to 10 mice per group) to the group of mice untreated with the drug (C, 10 mice per group). The daily dosage of IL-2 is shown by the weight (μg) of the drug per mouse, and the daily dosage of 5'-DFUR is also shown by the weight (μg) of the drug per mouse. Results obtained by giving IL-2 alone, 5'-DFUR alone and a combination of IL-2 and 5'-DFUR of the present invention are shown in Table 5.

TABLE 5

| Drug | Dosage (μg/ mouse) | Number of mice | Survival time (days) | average (median) | T/C (%) |
|---|---|---|---|---|---|
| Untreated control | | 10 | 37, 38, 38, 40, 40, 37, 38, 38, 41, 48 | 38.4 | |
| IL-2 | 20 | 5 | 41, 42, 50, 54, 55 | 50.5 | 132 |
| 5'-DFUR | 2000 | 5 | 56, 59, 62, 63, 63 | 62.5 | 163 |
| 5'-DFUR + IL-2 | | 10 | 65, 68, 85, 89, 97, 78, 79, 80, 83, 84 | 83.0 | 216 |

EXPERIMENTAL EXAMPLE 6

Examination of Survival Effect to Subcutaneously Implanted Tumor by Combination of 5'-DFUR and IL-2 with Another Anticancer Agent Tissue gruel of colic cancer No. 26 prepared similarly with Experimental Example 1 was subcutaneously implanted in femoral regions of female BALB/c mice with a body weight of about 25 g. 5'-DFUR and IL-2 were given once a day for 4 continuous days each week starting on the 20th day after the tumor implantation. This administration was repeated for 4 weeks. 5'-DFUR was orally given, and IL-2 was subcutaneously given to abdominal region opposite to the tumor-implanted site as with Experimental Example 1. An anticancer agent, MMC, was intravenously given to the mice 7, 24, 31 and 38 days after the tumor implantation. The dosage of each drug is shown by the weight (μg) per mouse. Even when 5'-DFUR and IL-2 of the present invention were given after the tumors had grown, excellent survival effect could be exhibited by the combinations with the additional anticancer agent. Results (the experiment was repeated twice) are shown in Table 6.

TABLE 6

| Drug | Dosage (μg/ mouse) | Number of mice | Survival time (days) | average (median) | T/C (%) |
|---|---|---|---|---|---|
| Untreated control | | 5 | 35, 37, 37, 38, 39 | 37.5 | |
| 5'-DFUR + IL-2 | 2000 20 | 5 | 49, 54, 56, 59, 79 | 56.5 | 151 |
| MMC + 5'-DFUR + IL-2 | 60 2000 20 | 5 | 65, 70, 79, 85, 88 | 79.5 | 212 |
| Untreated control | | 5 | 34, 37, 40, 40, 46 | 40.0 | |
| 5'-DFUR + IL-2 | 2000 20 | 5 | 62, 62, 62, 75, 95 | 62.5 | 156 |
| MMC + 5'-DFUR + IL-2 | 60 2000 20 | 5 | 76, 85, 91, 96, 96 | 91.5 | 229 |

EXAMPLE 1

Preparation for injection:

| | |
|---|---|
| IL-2 | 30 mg |
| 5'-DFUR | 6000 mg |
| Lactose | 170 mg |
| HPC-L (oxypropyl cellulose) | 10 mg |
| Total | 6210 mg |

The respective components were mixed at the above ratio, and then dissolved in distilled water for injection or in physiological saline. Human serum albumin (HSA)

was added thereto to a concentration of 0.5%, followed by filtration using a membrane filter having a pore size of 0.22 μm. One ml portions of the resulting filtrate were dispensed into respective vial bottles and lyophilized to prepare an antitumor agent for injection. This preparation for injection is dissolved in 5 ml of distilled water for injection when using it.

EXAMPLE 2

Preparation for injection:

| IL-2 | 30 mg |
|---|---|
| 5'-DFUR | 6000 mg |
| Lactose | 170 mg |
| Sodium lauryl sulfate | 1000 mg |
| Total | 7200 mg |

The respective components were mixed at the above ratio, and then dissolved in distilled water for injection or in physiological saline. Human serum albumin (HSA) was added thereto to a concentration of 0.5%, followed by filtration using a membrane filter having a pore size of 0.22 μm. One ml portions of the resulting filtrate were dispensed into respective vial bottles and lyophilized to prepare an antitumor agent for injection. This preparation for injection is dissolved in 5 ml of distilled water for injection when using it.

EXAMPLE 3

Preparation for injection:

| IL-2 | 5 mg |
|---|---|
| 5'-DFUR | 60,000 mg |
| Lactose | 200 mg |
| HPC-L (oxypropyl cellulose) | 100 mg |
| Total | 60,305 mg |

The respective components were mixed at the above ratio, and then dissolved in 1000 ml of distilled water or physiological saline for injection. Human serum albumin (HSA) was added thereto to a concentration of 0.5%, followed by filtration using a membrane filter having a pore size of 0.22 μm. Ten ml portions of the resulting filtrate were dispensed into respective vial bottles and lyophilized to prepare an antitumor agent for injection. This preparation for injection is dissolved in 10 ml of distilled water for injection when using it.

EXAMPLE 4

Preparation for injection:

| IL-2 | 10 mg |
|---|---|
| 5'-DFUR | 120,000 mg |
| Lactose | 200 mg |
| Sodium lauryl sulfate | 1,000 mg |
| Total | 121,210 mg |

The respective components were mixed at the above ratio, and then dissolved in 1000 ml of distilled water or physiological saline for injection. Human serum albumin (HSA) was added thereto to a concentration of 0.5%, followed by filtration using a membrane filter having a pore size of 0.22 μm. Ten ml portions of the resulting filtrate were dispensed into respective vial bottles and lyophilized to prepare an antitumor agent for injection. This preparation for injection is dissolved in 10 ml of distilled water for injection when using it.

EXAMPLE 5

Kit for injection preparation:

| [A] IL-2 | 10 mg |
|---|---|
| Lactose | 85 mg |
| HPC-L (oxypropyl cellulose) | 5 mg |
| Total | 100 mg |

The three components were mixed at the above ratio, and then dissolved in 1000 ml of distilled water or physiological saline for injection. Human serum albumin (HSA) was added thereto to a concentration of 0.5%, followed by filtration using a membrane filter having a pore size of 0.22 μm. Five ml portions of the resulting filtrate were dispensed aseptically into respective vial bottles and lyophilized to prepare a kit A.

| [B] 5'-DFUR | 120,000 mg |
|---|---|
| Sodium lauryl sulfate | 20,000 mg |
| Total | 140,000 mg |

The respective components were mixed at the above ratio, and then dissolved in 1000 ml of distilled water or physiological saline for injection, followed by filtration using a membrane filter having a pore size of 0.22 μm. Five ml portions of the resulting filtrate were dispensed aseptically into respective vial bottles and lyophilized to prepare a kit B.

| [C] Distilled water for injection | 10 mg |
|---|---|

The kit A is dissolved with the kit C and then the kit B is dissolved therein to obtain a solution for injection when using the kit. Alternatively, the kit B is dissolved with the kit C and then the kit A is dissolved therein to obtain a solution for injection when using the kit.

Alternatively, the kit A and the kit B is dissolved with the kit C respectively, to prepare two solutions for injection, a kit A solution and a kit B solution, which are administered separately at the same time or at an interval.

The following references, which are referred to for their disclosures at various points in this application, are incorporated herein by reference.

J. Immunol., 125, 1904 (1980)
Cancer and Chemotherapy 12(1), 2044 (1985)
Cancer and Chemotherapy 13, 977 (1986)
New England J. Med. 316, 889 (1987)
European Patent Publication No. 91539
Japanese Patent Unexamined Publication No. 60-126088/1985
Japanese Patent Unexamined Publication No. 59-93093/1984 which corresponds to U.S. Pat. No.4,518,584
Japanese Patent Unexamined Publication No. 60-226821/1985 which corresponds to European Publication No. 154316)
Japanese Patent Unexamined Publication No. 60-115528/1985 which corresponds to European Publication No. 145390

Japanese Patent Unexamined Publication No. 61-78799/1986 which corresponds to European Pulication No. 176299

J. Med. Chem. 22, 1330-1335 (1979)

Cancer and Chemotherapy 15(5), 1747-1754 (1988)

amount of interleukin-2 (IL-2) and 5'-deoxy-5-flourouridine (5'-DFUR) or a salt thereof in a pharmaceutical carrier, wherein the ratio of 5'-DFUR or a salt thereof to IL-2 is from about 0.1 to about 100 mg of 5'-DFUR or a salt thereof per 10 μg of protein of IL-2.

---

I claim:

1. A method for immunostimulating a mammal, which comprises administering to the mammal an effective amount of interleukin-2 (IL-2) and 5'-deoxy-5-fluorouridine (5'-DFUR) or a salt thereof, wherein the ratio of 5'-DFUR to IL-2 is from about 0.1 to about 100 mg of 5'-DFUR or a salt thereof per 10 μg of protein of IL-2.

2. A method in accordance with claim 1, wherein the mammal contains at least one tumor.

3. A method in accordance with claim 1, wherein the method comprises administering to the mammal interleukin-2 and 5'-deoxy-5-fluorouridine or a salt thereof concurrently.

4. A method in accordance with claim 1, wherein the method comprises administering to the mammal interleukin-2 and 5'-deoxy-5-fluorouridine or a salt thereof separately.

5. A method in accordance with claim 1, wherein the ratio of interleukin-2 and 5'-deoxy-5-fluorouridine or a salt thereof on the basis of 10 μg of protein of IL-2 is from about 1 to about 50 mg of 5'-deoxy-5-fluorouridine or a salt thereof.

6. A pharmaceutical composition for immunostimulating a mammal which comprises an effective amount of interleukin-2 (IL-2) and 5'-deoxy-5-flourouridine (5'-DFUR) or a salt thereof in a pharmaceutical carrier, wherein the ratio of 5'-DFUR or a salt thereof to IL-2 is from about 0.1 to about 100 mg of 5'-DFUR or a salt thereof per 10 μg of protein of IL-2.

7. A composition in accordance with claim 6, wherein the composition comprises mixing interleukin-2 and 5'-deoxy-5-fluorouridine or a salt thereof.

8. A kit of pharmaceutical preparations for immunostimulating a mammal, which comprises a pharmaceutical preparation of interleukin-2 and a pharmaceutical preparation of 5'-deoxy-5-fluorouridine or a salt thereof.

9. A composition in accordance with claim 6, wherein the ratio of interleukin-2 and 5'-deoxy-5-fluorouridine or a salt thereof on the basis of 10 μg of protein of IL-2 is from about 1 to about 50 mg of 5'-deoxy-5-fluorouridine or a salt thereof.

10. A composition in accordance with claim 6, further containing another immunotherapeutic agent in which said another immunotherapeutic agent is selected from the group consisting of microorganisms, bacterial cell wall skeletal components, immunologically active natural polysaccharides, cytokines obtained by genetic engineering technique and natural cytokines.

11. A composition in accordance with claim 10, in which said immunologically active natural polysaccharide is lenthinan or schizophyllan.

12. A composition in accordance with claim 10, in which said bacterial cell wall skeletal component is a muramyldipeptide derivative.

13. A composition in accordance with claim 10, in which said microorganism is a lactic acid bacterium.

14. A composition in accordance with claim 10, in which said cytokine is selected from natural cytokines and cytokines obtained by genetic engineering technique and is an interferon or colony stimulating factors.

15. A composition in accordance with claim 6 wherein said interleukin-2 contains a biological or immunological active fragment.

16. A method in accordance with claim 1 wherein said interleukin-2 contains a biological or immunological active fragment.

17. The method of claim 1, wherein the IL-2 has Sequence ID NO:1.

18. The composition of claim 6, wherein the IL-2 has Sequence ID NO:1.

19. The kit of claim 8, wherein the IL-2 has Sequence ID NO:1.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 133 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Ala Pro Thr Ser Ser Ser Thr Lys Lys Thr Gln Leu Gln Leu Glu His
 1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Glu Leu Lys
        50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
    130
```